(12) United States Patent
Kobayashi et al.

(10) Patent No.: US 8,660,632 B2
(45) Date of Patent: Feb. 25, 2014

(54) MEDICAL IMAGE PROCESSING APPARATUS, X-RAY CT APPARATUS, MRI APPARATUS, ULTRASOUND DIAGNOSTIC IMAGING APPARATUS, AND MEDICAL IMAGE PROCESSING METHOD

(75) Inventors: Hideaki Kobayashi, Otawara (JP); Hitoshi Yamagata, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 1170 days.

(21) Appl. No.: 12/577,863

(22) Filed: Oct. 13, 2009

(65) Prior Publication Data
US 2010/0094118 A1 Apr. 15, 2010

(30) Foreign Application Priority Data
Oct. 15, 2008 (JP) ................. P2008-266351

(51) Int. Cl.
*A61B 5/05* (2006.01)

(52) U.S. Cl.
USPC ........... 600/407; 600/426; 600/410; 600/424; 600/411; 600/437; 382/128

(58) Field of Classification Search
USPC ............... 600/407, 410, 424, 426, 437, 441; 382/128
See application file for complete search history.

(56) References Cited

U.S. PATENT DOCUMENTS 8,208,699 B2 * 6/2012 Hay et al. ..................... 382/128

OTHER PUBLICATIONS

Makiko Hayashi, et al., "Correlation Between the Blood Supply and Grade of Malignancy of Hepatocellular Nodules Associated with Liver Cirrhosis: Evaluation by CT During Intraarterial Injection of Contrast Medium". ARJ:172, Apr. 1999, pp. 969-976.

* cited by examiner

*Primary Examiner* — Joel Lamprecht
(74) *Attorney, Agent, or Firm* — Oblon, Spivak, McClelland, Maier & Neustadt, L.L.P.

(57) ABSTRACT

A medical image processing apparatus has a parameter calculating unit, a storage unit, and an image generating unit. The parameter calculating unit analyzes data of a plurality of time-series medical images, each containing an image of an organ having a functional blood vessel and a feeding blood vessel, and calculates a parameter based on at least a blood volume in the feeding blood vessel. The storage unit stores in advance a table that associates parameters with degrees of a cancer progression of the organ. The image generating unit refers to the table, obtains a degree of the cancer progression corresponding to the calculated parameter, and generates an image to which the obtained degree is applied on a region-by-region basis.

18 Claims, 7 Drawing Sheets

MEDICAL IMAGE PROCESSING APPARATUS, X-RAY CT APPARATUS, MRI APPARATUS, ULTRASOUND DIAGNOSTIC IMAGING APPARATUS, AND MEDICAL IMAGE PROCESSING METHOD

BACKGROUND OF THE INVENTION

1. Field of the Invention

The present invention relates to a medical image processing apparatuses, an X-ray computed tomography (CT) apparatus, a magnetic resonance imaging (MRI) apparatus, an ultrasound diagnostic imaging apparatus, and a medical image processing method used to examine hepatic functions with perfusion technique.

2. Description of the Related Art

As an example of techniques used to examine hepatic functions with an X-ray CT apparatus, there is a CT-perfusion technique which involves quantifying parameters of a hepatic blood flow using an iodine contrast agent as a tracer. Examples of images obtained by calculation based on the CT-perfusion technique are shown in FIG. 3.

As a hepatocellular cancer progresses, a hepatic blood flow slows down and a hepatic arterial fraction (i.e., hepatic arterial blood volume/(hepatic arterial blood volume+portal venous blood volume)) increases, as shown in FIG. 4. The increase in hepatic arterial fraction indicates that although a decrease in portal venous blood volume leads to a decrease in total hepatic blood volume, the decrease is compensated for by the increase in blood volume in the hepatic artery serving as a feeding blood vessel, the increase being caused by the effect of the hepatocellular cancer.

Nutrients are supplied to normal hepatic cells at a hepatic-arterial-blood-volume to portal-venous-blood-volume ratio of 2:8, that is, at a hepatic arterial fraction of 20%. However, it has been reported that in early stages of cancer, such as a regenerative nodule stage and an adenoma stage, a portal venous blood volume and a hepatic arterial blood volume decrease (ischemia occurs) in the affected area, and as a stage (degree of cancer progression) progresses and a plethoric hepatocellular cancer stage approaches, the hepatic arterial blood volume increases while the portal venous blood volume decreases in the affected area (see, e.g., a following Document 1).

Document 1: Makiko Hayashi, Osamu Matsui, et al. "Correlation Between the Blood Supply and Grade of Malignancy of Hepatocellular Nodules Associated with Liver Cirrhosis: Evaluation by CT During Intraarterial Injection of Contrast Medium" AJR: 172, April 1999: 969-976

Thus, since the hepatic arterial fraction increases as the plethoric hepatocellular cancer stage approaches, it is possible to diagnose a cancer in advanced stages, such as an early liver cancer stage and a plethoric hepatocellular cancer stage, because an apparent increase in hepatic arterial fraction can be observed.

However, in the early stages, such as the regenerative nodule stage and the adenoma stage, since there is an occurrence of ischemia in which the portal venous blood volume and the hepatic arterial blood volume decrease at substantially the same rate, the hepatic arterial fraction tends to be determined to be 20%, which is the same as that in normal (unaffected) areas. As a result, it is difficult to make early detection of hepatic tumor and stage determination of cancer in early stages.

SUMMARY OF THE INVENTION

The present invention has been made in view of the circumstances described above. An object of the present invention is to provide a medical image processing apparatus, an X-ray CT apparatus, an MRI apparatus, an ultrasound diagnostic imaging apparatus, and a medical image processing method for improved diagnostic accuracy in determining the degree of the cancer progression.

To solve the above-described problems, the present invention provides the medical image processing apparatus has: a parameter calculating unit configured to analyze data of a plurality of time-series medical images, each containing an image of an organ having a functional blood vessel and a feeding blood vessel, and to calculate a parameter based on at least a blood volume in the feeding blood vessel; a storage unit configured to store in advance a table that associates parameters with degrees of a cancer progression of the organ; and an image generating unit configured to refer to the table, to obtain a degree of the cancer progression corresponding to the calculated parameter, and to generate an image to which the obtained degree is applied on a region-by-region basis.

To solve the above-described problems, the present invention provides the X-ray CT apparatus has the medical image processing apparatus.

To solve the above-described problems, the present invention provides the MRI apparatus has the medical image processing apparatus.

To solve the above-described problems, the present invention provides the ultrasound diagnostic imaging apparatus has the medical image processing apparatus.

To solve the above-described problems, the present invention provides the medical image processing method has: a parameter calculating step of analyzing data of a plurality of time-series medical images, each containing an image of an organ having a functional blood vessel and a feeding blood vessel, and of calculating a parameter based on at least a blood volume in the feeding blood vessel; a storing step of storing in advance a table that associates parameters with degrees of a cancer progression of the organ; and an image generating step of referring to the table, of obtaining a degree of the cancer progression corresponding to the calculated parameter, and of generating an image to which the obtained degree is applied on a region-by-region basis.

DESCRIPTION OF THE PREFERRED EMBODIMENTS

Embodiments of a medical image processing apparatus, an X-ray CT apparatus, an MRI apparatus, an ultrasound diagnostic imaging apparatus, and a medical image processing method according to the present invention will now be described with reference to the attached drawings.

Figure 1:
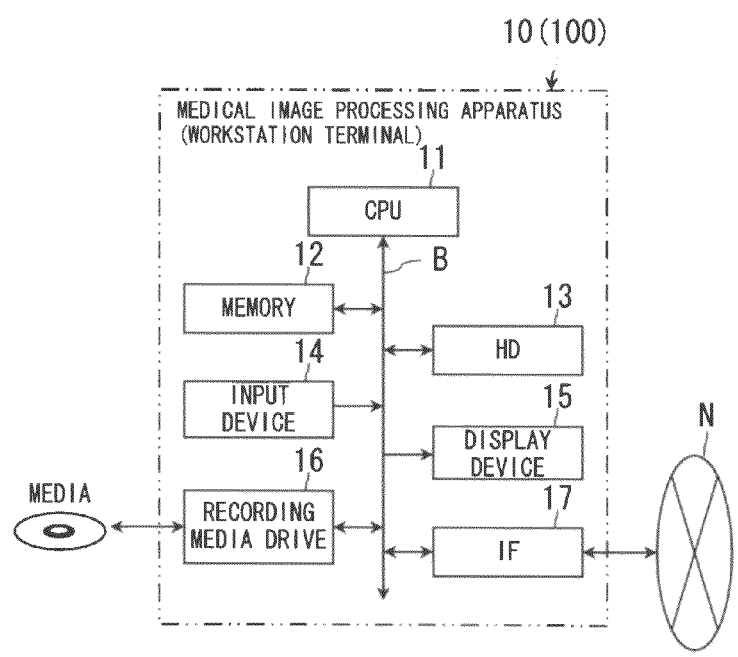
FIG. 1 is a schematic diagram showing a configuration of a medical image processing apparatus of the present embodiment.

FIG. 1 is a schematic diagram showing a configuration of the medical image processing apparatus of the present embodiment.

FIG. 1 shows a workstation terminal 100 as an example of a medical image processing apparatus 10 of the present embodiment. The workstation terminal 100 mainly includes basic hardware components, such as a central processing unit (CPU) 11 serving as a control device, a memory 12, a hard disk (HD) 13, an input device 14, a display device 15, a recording media drive 16, and an interface (IF) 17. The CPU 11 and other components included in the workstation terminal 100 are connected to each other via a bus B serving as a common signal transmission path.

The CPU 11 is a control device configured as a large-scale integrated circuit (LSI) formed by enclosing a semiconductor electronic circuit in a package having a plurality of terminals. The CPU 11 executes a program stored in the memory 12. Alternatively, a program stored in the HD 13, or a program transferred from a network N, received by the IF 17, and installed on the HD 13 may be loaded into the memory 12 and executed by the CPU 11.

The memory 12 is a storage device serving as a read-only memory (ROM), a random-access memory (RAM), etc. The memory 12 is used for initial program loading (IPL), and for storing a basic input/output system (BIOS) and data. Additionally, the memory 12 serves as work memory of the CPU 11 and a temporary data storage area.

The HD 13 is a storage device having a configuration where metal disks to which magnetic material is applied or evaporated are unremovably placed inside a reader (not shown). The HD 13 stores programs (including an operating system (OS) as well as application programs) installed onto the workstation terminal 100. At the same time, the HD 13 causes the OS to provide a graphical user interface (GUI). The GUI allows information containing many graphical elements to be displayed to the operator, so that the operator can perform basic operations with the input device 14.

The input device 14 includes pointing devices (e.g., a keyboard and a mouse) that are operable by the operator, such as a person who performs diagnostic examinations.

The display device 15 is a cathode ray tube (CRT) display, a liquid crystal display, or the like.

The recording media drive 16 is configured to allow insertion and removal of a portable recording medium. The recording media drive 16 reads data (including a program) recorded in a recording medium and outputs the read data to the bus B. Also, the recording media drive 16 writes data supplied via the bus B to the recording medium. Examples of the recording medium include a flexible disk (FD), a compact disk-read only memory (CD-ROM), a compact disk recordable (CD-R), a compact disk rewritable (CD-RW), a magneto-optical (MO) disk, a digital versatile disk (DVD), a digital versatile disk-recordable (DVD-R), and a magnetic disk.

The IF 17 is a connector that conforms to parallel connection specifications or serial connection specifications. The IF 17 performs communication control in accordance with an appropriate standard. The IF 17 thus allows the workstation terminal 100 to be connected to the network N.

Figure 2:
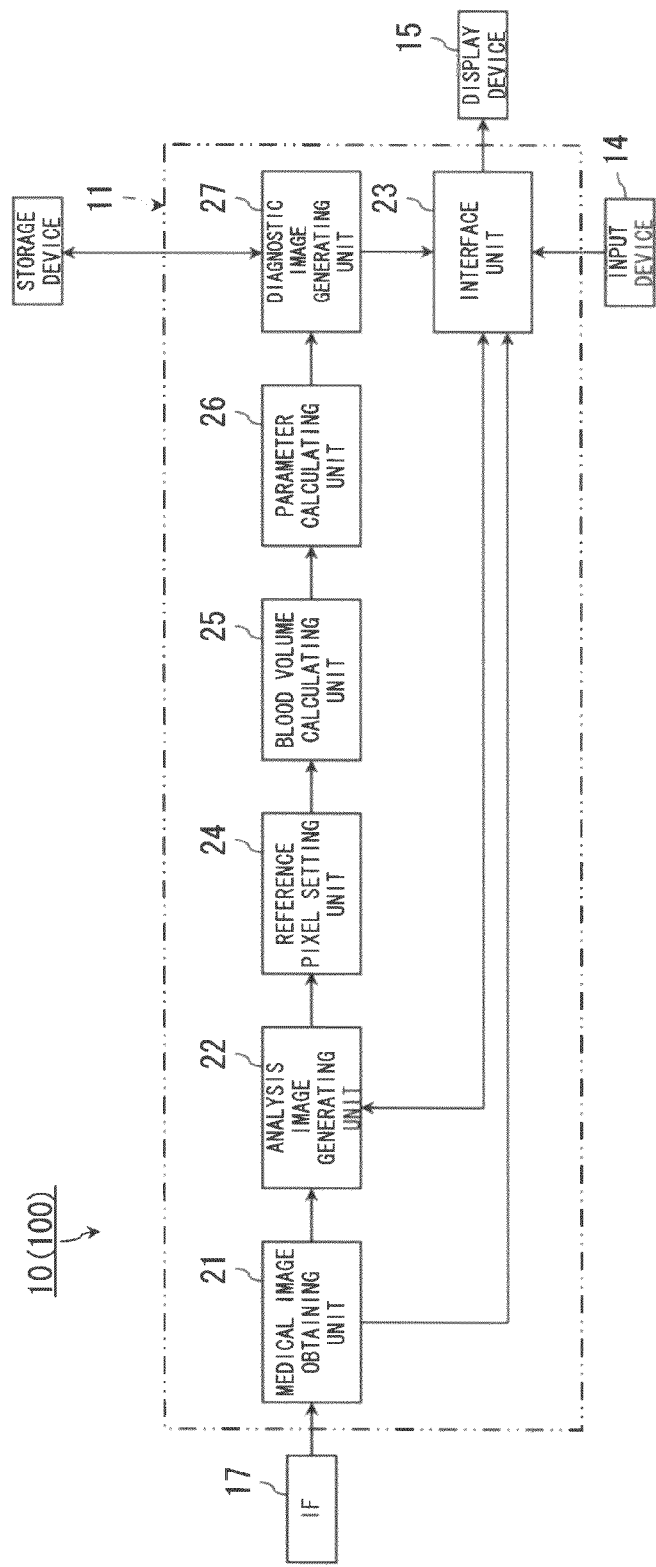
FIG. 2 is a block diagram showing functions of the medical image processing apparatus of the present embodiment.

FIG. 2 is a block diagram showing functions of the medical image processing apparatus 10 of the present embodiment.

When the CPU 11 shown in FIG. 1 executes a program, the workstation terminal 100, which is the medical image processing apparatus 10, functions as a medical image obtaining unit 21, an analysis image generating unit 22, an interface unit 23, a reference pixel setting unit 24, a blood volume calculating unit 25, a parameter calculating unit 26, and a diagnostic image generating unit 27. Alternatively, the workstation terminal 100 may include the medical image obtaining unit 21, the analysis image generating unit 22, the interface unit 23, the reference pixel setting unit 24, the blood volume calculating unit 25, the parameter calculating unit 26, and the diagnostic image generating unit 27 as a circuit.

The medical image obtaining unit 21 uses, for example, patient information (such as a patient ID) and the name of a body part as keys to obtain data of a plurality of time-series medical images, via the IF 17, from an image server (not shown) included in picture archiving and communication systems (PACS). For example, when a liver is selected, for a patient, as an organ having a functional blood vessel and a feeding blood vessel, the medical image obtaining unit 21 obtains data of a plurality of time-series medical images, each containing an image of the liver. The following description will discuss the case where the medical image obtaining unit 21 obtains data of a plurality of time-series medical images, each containing an image of a liver having a portal vein serving as a functional blood vessel and a hepatic artery serving as a functional blood vessel. Note that examples of an organ having a functional blood vessel and a feeding blood vessel include a lung field as well as a liver.

The analysis image generating unit 22 analyzes data of a plurality of time-series CT images obtained by the medical image obtaining unit 21, and generates a hepatic blood flow (HBF) image, a hepatic blood volume (HBV) image, a mean transit time (MTT) image, and a hepatic arterial fraction (HAF) image serving as functional images. The CT images obtained by the medical image obtaining unit 21 and the functional images generated by the analysis image generating unit 22 are displayed via the interface unit 23 on the display device 15.

Figure 3:
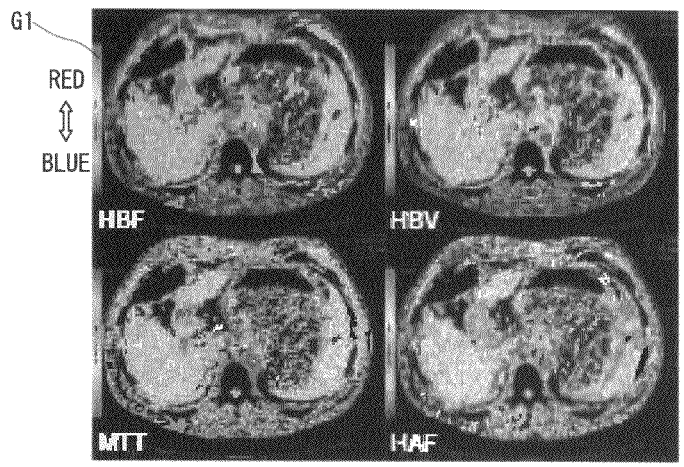
FIG. 3 is a diagram showing examples of functional images.

FIG. 3 is a diagram showing examples of functional images generated by the analysis image generating unit 22.

The functional images shown in FIG. 3 are obtained by assigning one of 256 colors in a color gradation chart (from blue to red) G1 depending on a largeness of a one-dimensional parameter every pixel, and arranging a selected color of the colors in the pixel. An HAF image is generated by assigning one of 256 colors in the color gradation chart G1 to a hepatic arterial fraction (i.e., hepatic arterial blood volume/ (hepatic arterial blood volume+portal venous blood volume)) obtained for every pixel of a CT image.

The interface unit 23 shown in FIG. 2 is an interface, such as the GUI. The GUI allows information containing many graphical elements to be displayed on the display device 15 to the user, so that the use can perform basic operations with the input device 14.

The reference pixel setting unit 24 sets a reference pixel (or region representing a reference pixel) selected from a group of pixels constituting the function image such as the HAF image generated by the analysis image generating unit 22. The selection of a reference pixel is made by the operator using the input device 14. Specifically, while viewing CT images and functional images displayed on the display device 15, the operator selects a reference pixel by clicking (input) on a displayed HAF image via the interface unit 23. Thus, the reference pixel is set in response to the operator's clicking (input). Generally, of pixels constituting the HAF image, a pixel which is assumed to contain the image of normal hepatic cells in the multistage carcinogenic process is selected as a reference pixel by the operator. Alternatively, the reference pixel setting unit 24 may set a reference pixel by converting a pixel selected on a 3D image or a multi-planar reconstruction (MPR) image obtained by the medical image obtaining unit 21 into that on the HAF image.

The blood volume calculating unit 25 calculates a hepatic arterial blood volume and a portal venous blood volume for the reference pixel set by reference pixel setting unit 24. At the same time, the blood volume calculating unit 25 calculates a hepatic arterial blood volume and a portal venous blood volume for every non-reference pixel (or region representing every non-reference pixel), which is not the reference pixel set by the reference pixel setting unit 24.

The parameter calculating unit 26 compares, for each of the non-reference pixels, the hepatic arterial blood volume calculated for the non-reference pixel by the blood volume calculating unit 25 with the hepatic arterial blood volume calculated for the reference pixel by the blood volume calculating unit 25, so as to determine a hepatic arterial blood volume comparison value (i.e., a hepatic arterial blood volume ratio or a hepatic arterial blood volume difference). For example, for each of the non-reference pixels, the parameter calculating unit 26 calculates a hepatic arterial blood volume ratio indicating a ratio of the hepatic arterial blood volume for the non-reference pixel to that for the reference pixel.

Also, the parameter calculating unit 26 compares, for each of the non-reference pixels, the portal venous blood volume calculated for the non-reference pixel by the blood volume calculating unit 25 with the portal venous blood volume calculated for the reference pixel by the blood volume calculating unit 25, so as to determine a portal venous blood volume comparison value (i.e., a portal venous blood volume ratio or a portal venous blood volume difference). For example, for each of the non-reference pixels, the parameter calculating unit 26 calculates a portal venous blood volume ratio indicating a ratio of the portal venous blood volume for the non-reference pixel to that for the reference pixel.

Note that the parameter calculating unit 26 calculates a hepatic arterial blood volume ratio and a portal venous blood volume ratio in the examples described above, the parameter calculating unit 26 may calculate a hepatic arterial blood volume difference indicating a difference between the hepatic arterial blood volume for the reference pixel and that for each of the non-reference pixels, or may calculate a portal venous blood volume difference indicating a difference between the portal venous blood volume for the reference pixel and that for each of the non-reference pixels.

Figure 4:
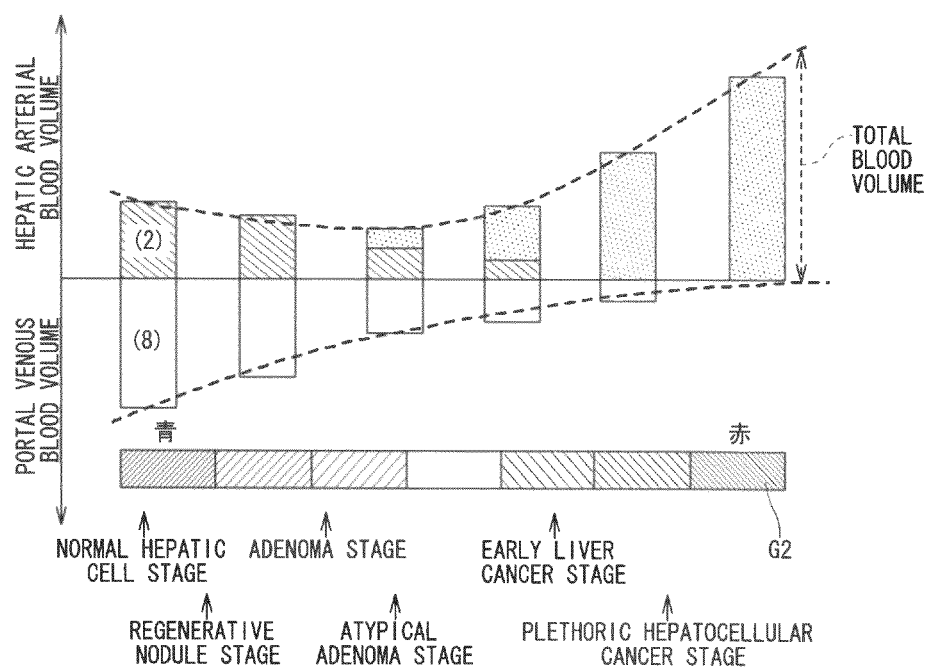
FIG. 4 is a diagram showing a relationship between a multistage carcinogenic process and a color gradation chart representing the multistage carcinogenic process.

A storage device, such as the memory 12, stores in advance a table that associates two-dimensional parameters with corresponding 256 colors in a color gradation chart G2 (from blue to red) representing the multistage carcinogenic process shown in FIG. 4, the two-dimensional parameters each representing a hepatic arterial blood volume ratio and a portal venous blood volume ratio.

FIG. 4 is a diagram showing a relationship between the multistage carcinogenic process and the color gradation chart G2 representing the multistage carcinogenic process.

As shown in FIG. 4, for example, when a two-dimensional parameter represents a hepatic arterial blood volume ratio and a portal venous blood volume ratio that are both substantially one, the two-dimensional parameter is associated with blue (stage: normal hepatic cell) in the color gradation chart G2. For example, when a two-dimensional parameter represents a portal venous blood volume ratio of substantially "0" and a hepatic arterial blood volume ratio of substantially "2", the two-dimensional parameter is associated with red (stage: plethoric hepatocellular cancer) in the color gradation chart G2.

The diagnostic image generating unit 27 shown in FIG. 2 refers to a two-dimensional parameter representing the hepatic arterial blood volume ratio and the portal venous blood volume ratio calculated for each of the non-reference pixels by the parameter calculating unit 26, the two-dimensional parameter being contained in the table stored in the storage device, obtains from the color gradation chart G2 a color corresponding to the two-dimensional parameter for each of the non-reference pixels, and generates a diagnostic image representing the multistage carcinogenic process on the basis of the obtained color. The diagnostic image generating unit 27 assigns an appropriate color to every non-reference pixel to generate the diagnostic image. As for the reference pixel, both a hepatic arterial blood volume ratio and a portal venous blood volume ratio are set to "1" (blue). The diagnostic image generated by the diagnostic image generating unit 27 is displayed via the interface unit 23 on the display device 15.

Nutrients are supplied to normal hepatic cells at a hepatic-arterial-blood-volume to portal-venous-blood-volume ratio of 2:8. However, in early stages of cancer, such as a regenerative nodule stage and an adenoma stage, the portal venous blood volume and the hepatic arterial blood volume decrease (ischemia occurs) in the affected area. Then, as a stage (degree of cancer progression) progresses and the plethoric hepatocellular cancer stage approaches, the hepatic arterial blood volume increases and the portal venous blood volume decreases in the affected area. In early stages, such as in the regenerative nodule stage and the adenoma stage, since there is an occurrence of ischemia in which the portal venous blood volume and the hepatic arterial blood volume decrease at substantially the same rate, the hepatic arterial fraction tends to be determined to be 20%, which is the same as that in normal (unaffected) areas. As a result, it is difficult to make early detection of hepatic tumor and stage determination of cancer in early stages, on the basis of an HAF image obtained by assigning colors in the color gradation chart G1 shown in FIG. 3 representing the multistage carcinogenic process to corresponding hepatic arterial fractions.

Thus, a hepatic arterial blood volume in hepatic cells in a normal stage is compared with that in another stage, and a portal venous blood volume in hepatic cells in a normal stage is compared with that in another stage. These comparisons show that in early stages, such as the regenerative nodule stage and the adenoma stage, the hepatic arterial blood volume and the portal venous blood volume decrease as the multistage carcinogenic process proceeds from the normal hepatic cell stage. Therefore, the medical image processing apparatus 10 determines the ratio of a hepatic arterial blood volume for a non-reference pixel in an HAF image corresponding to the normal hepatic cell stage to a hepatic arterial blood volume for a reference pixel in the HAF image, and also determines the ratio of a portal venous blood volume for the non-reference pixel to a portal venous blood volume for the reference pixel. Then, the medical image processing apparatus 10 generates and displays a diagnostic image by assigning appropriate colors in the color gradation chart G2 representing the multistage carcinogenic process to two-dimensional parameters, each representing the ratios determined as described above. Thus, on the basis of the diagnostic image generated by the medical image processing apparatus 10, it is possible to make early detection of hepatic tumor and stage determination of cancer in early stages, such as the regenerative nodule stage and the adenoma stage in the multistage carcinogenic process.

Figure 5:
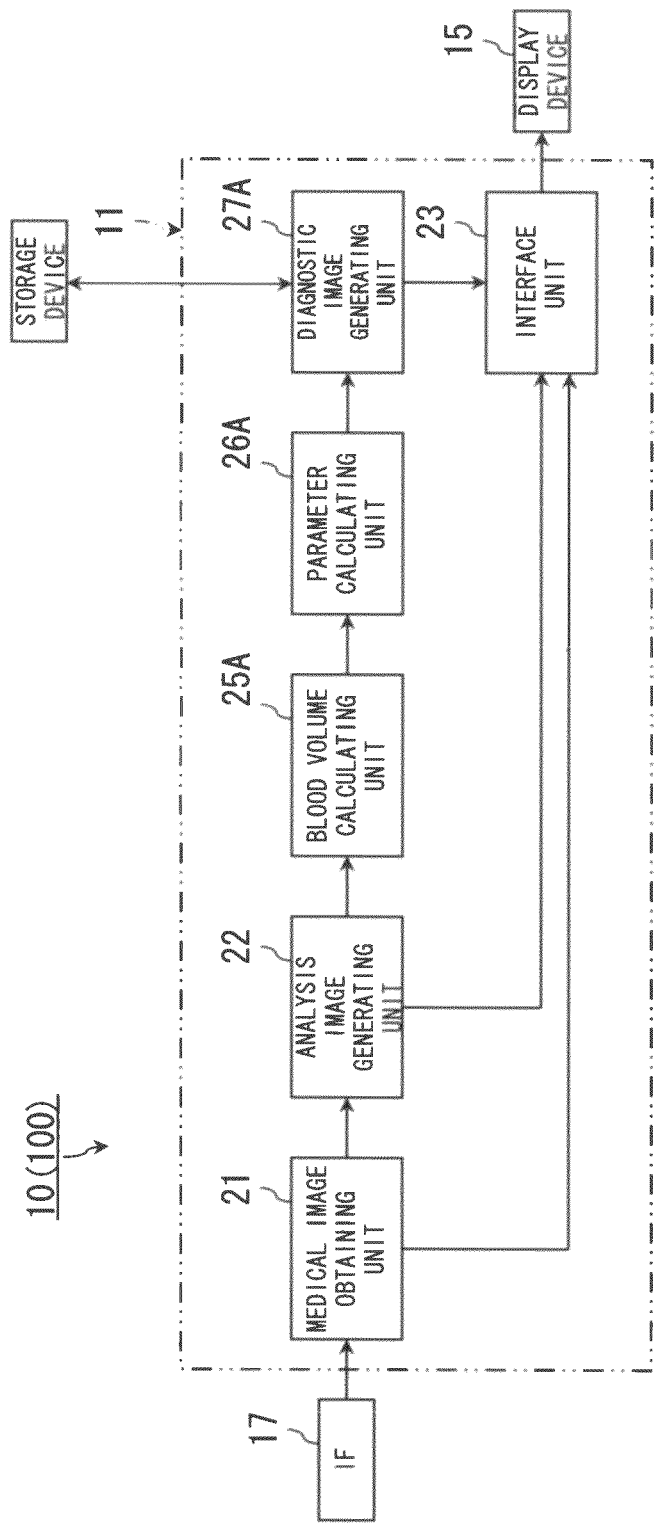
FIG. 5 is a block diagram showing a first modification of the medical image processing apparatus shown in FIG. 2.

FIG. 5 is a block diagram showing a first modification of the medical image processing apparatus 10 shown in FIG. 2.

When the CPU 11 shown in FIG. 1 executes a program, the workstation terminal 100, which is the medical image processing apparatus 10, functions as the medical image obtaining unit 21, the analysis image generating unit 22, the interface unit 23, a blood volume calculating unit 25A, a parameter calculating unit 26A, and a diagnostic image generating unit 27A. Alternatively, the workstation terminal 100 may include the medical image obtaining unit 21, the analysis image generating unit 22, the interface unit 23, the blood volume calculating unit 25A, the parameter calculating unit 26A, and the diagnostic image generating unit 27A as a circuit.

The blood volume calculating unit 25A calculates a hepatic arterial blood volume and a portal venous blood volume for every pixel (or region representing every pixel) constituting the functional image generated by the analysis image generating unit 22.

The parameter calculating unit 26A calculates, for each pixel, a product of the hepatic arterial blood volume and the portal venous blood volume calculated by the blood volume calculating unit 25A.

A storage device, such as the memory 12, stores in advance a table that associates one-dimensional parameters with corresponding colors in the color gradation chart G2 representing the multistage carcinogenic process shown in FIG. 4, the one-dimensional parameters each representing a product of the hepatic arterial blood volume and the portal venous blood volume.

The diagnostic image generating unit 27A refers to a one-dimensional parameter representing a product of the hepatic arterial blood volume and the portal venous blood volume calculated for each pixel by the parameter calculating unit 26A, the one-dimensional parameter being contained in the table stored in the storage device, obtains from the color gradation chart G2 a color corresponding the one-dimensional parameter for the pixel, and generates a diagnostic image representing the multistage carcinogenic process on the basis of the obtained color. The diagnostic image generating unit 27A assigns an appropriate color to every pixel to generate the diagnostic image. The diagnostic image generated by the diagnostic image generating unit 27A is displayed via the interface unit 23 on the display device 15.

Figure 6:
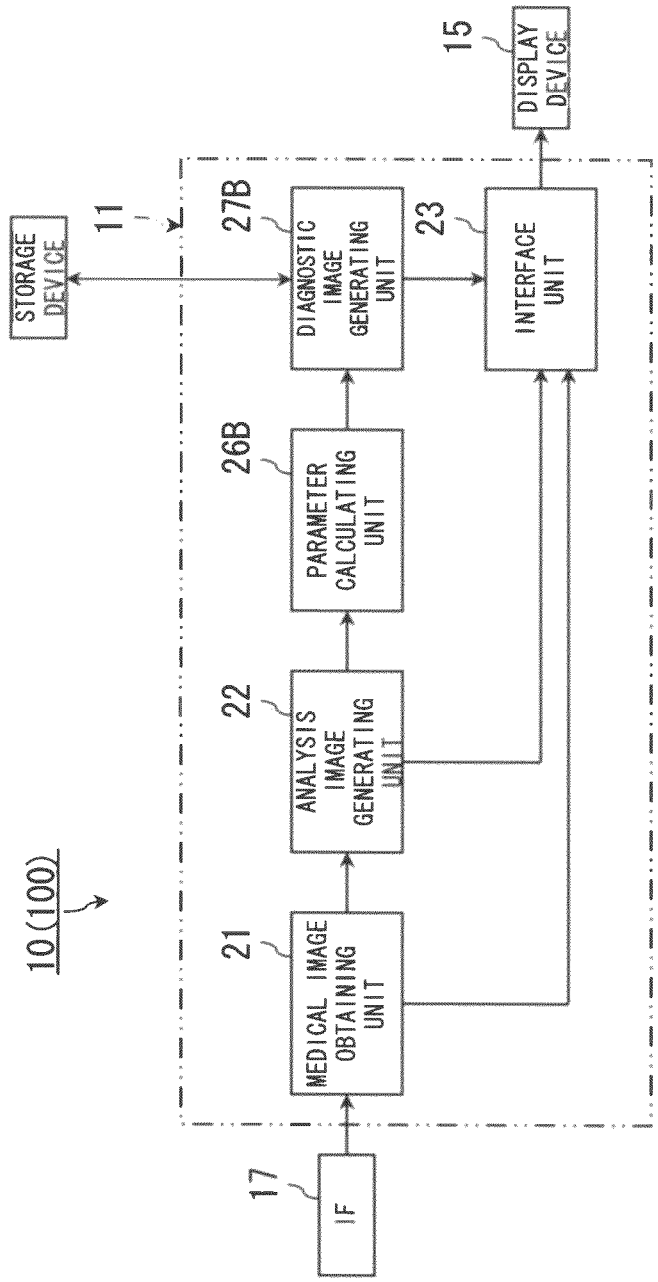
FIG. 6 is a block diagram showing a second modification of the medical image processing apparatus shown in FIG. 2.

FIG. 6 is a block diagram illustrating a second modification of the medical image processing apparatus 10 shown in FIG. 2.

When the CPU 11 shown in FIG. 1 executes a program, the workstation terminal 100, which is the medical image processing apparatus 10, functions as the medical image obtaining unit 21, the analysis image generating unit 22, the interface unit 23, a parameter calculating unit 26B, and a diagnostic image generating unit 27B. Alternatively, the workstation terminal 100 may include the medical image obtaining unit 21, the analysis image generating unit 22, the interface unit 23, the parameter calculating unit 26B, and the diagnostic image generating unit 27B as a circuit.

The parameter calculating unit 26B calculates a hepatic arterial blood volume for every pixel (or region representing every pixel) constituting the functional image generated by the analysis image generating unit 22.

A storage device, such as the memory 12, stores in advance a table that associates one-dimensional parameters with corresponding colors in the color gradation chart G2 representing the multistage carcinogenic process shown in FIG. 4, the one-dimensional parameters each representing a hepatic arterial blood volume.

The diagnostic image generating unit 27B refers to a one-dimensional parameter representing a hepatic arterial blood volume calculated for each pixel by the parameter calculating unit 26B, the one-dimensional parameter being contained in the table stored in the storage device; obtains from the color gradation chart G2 a color corresponding the one-dimensional parameter for the pixel; and generates a diagnostic image representing the multistage carcinogenic process on the basis of the obtained color. The diagnostic image generating unit 27B assigns an appropriate color to every pixel to generate the diagnostic image. The diagnostic image generated by the diagnostic image generating unit 27B is displayed via the interface unit 23 on the display device 15.

As described above, the workstation terminal 100 serving as the medical image processing apparatus 10 of the present embodiment is capable of generating and displaying a visible diagnostic image of a liver in early stages of the multistage carcinogenic process, such as the regenerative nodule stage and the adenoma stage. It is thus possible to achieve improved accuracy in diagnosing hepatocellular cancer.

Figure 7:
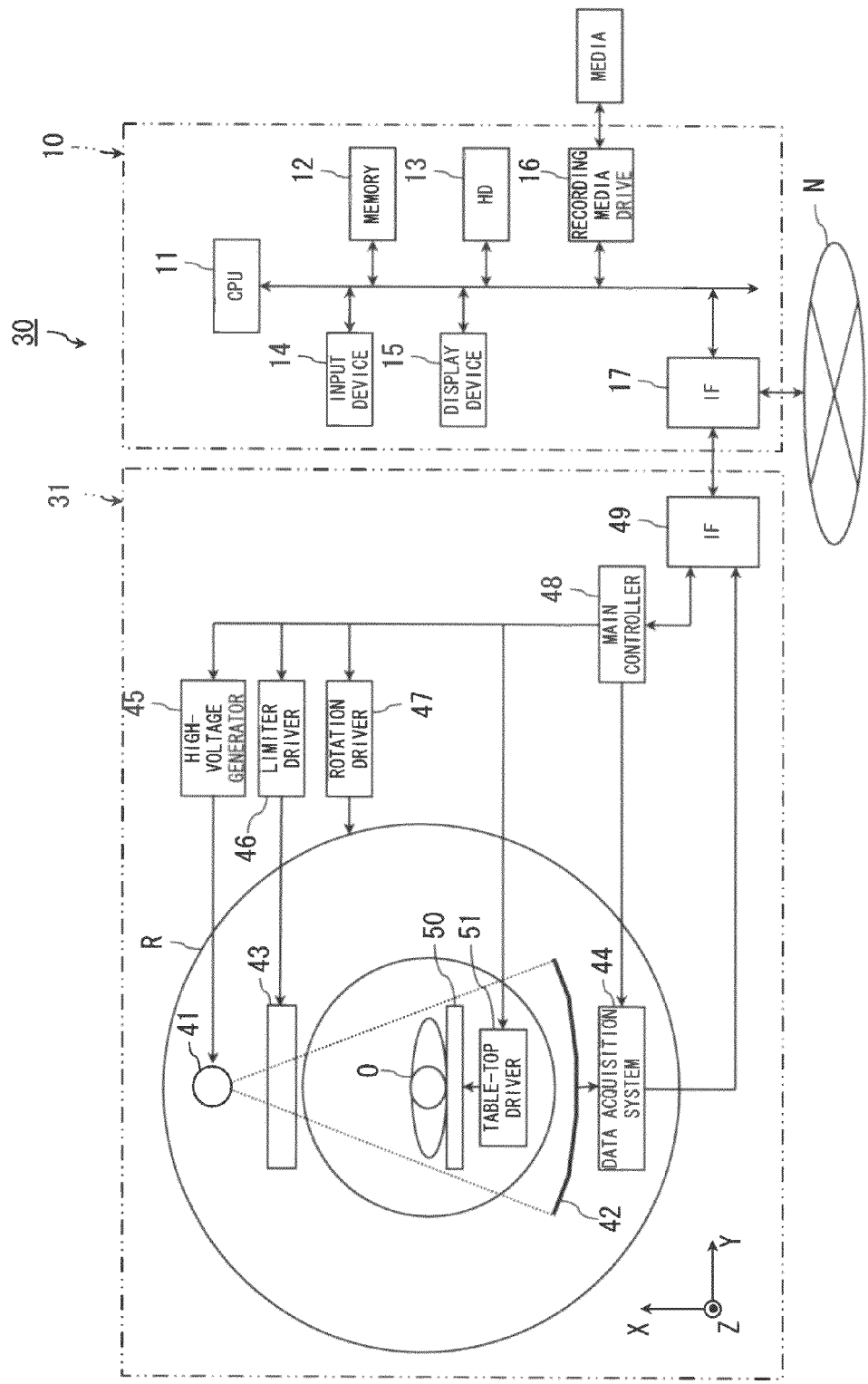
FIG. 7 is a schematic diagram showing a configuration of a medical imaging apparatus including the medical image processing apparatus of the present embodiment.

FIG. 7 is a schematic diagram showing a configuration of a medical imaging apparatus including the medical image processing apparatus 10 of the present embodiment.

FIG. 7 shows an X-ray CT apparatus 30 as an example of the medical imaging apparatus including the medical image processing apparatus 10 of the present embodiment. As shown, the X-ray CT apparatus 30 includes the medical image processing apparatus 10 and an imaging system 31. The imaging system 31 of the X-ray CT apparatus 30 is configured to generate projection data for generating data of a plurality of time-series CT images of a target body part of a patient (object to be examined) O, the target body part being a subject of imaging. Note that the medical imaging apparatus is not limited to the X-ray CT apparatus 30, but may be an MRI apparatus or an ultrasound diagnostic imaging apparatus for which the perfusion technique can be used.

The imaging system 31 includes an X-ray tube 41, an X-ray detector 42, a limiter 43, a data acquisition system 44, a high-voltage generator 45, a limiter driver 46, a rotation driver 47, a main controller 48, an IF 49, a table-top 50, and a table-top driver 51.

The X-ray tube 41, the X-ray detector 42, the limiter 43, and the data acquisition system 44 are provided in a rotating unit R on a mount device (not shown) of the imaging system 31. The rotating unit R is configured such that the X-ray tube 41 and the X-ray detector 42 can move about the patient O while being located opposite each other.

The X-ray tube 41 generates X-rays in accordance with tube voltage supplied from the high-voltage generator 45.

The X-ray detector 42 is a two-dimensional array detector, which may also be referred to as a multi-slice detector. Each X-ray detecting element of the X-ray detector 42 has, for example, a 0.5-mm-by-0.5-mm square detection surface. In the X-ray detector 42, for example, 916 X-ray detecting elements are arranged in a channel direction and at least 64 rows of the X-ray detecting elements are arranged in parallel along a slicing direction (i.e., along the direction of rows of the X-ray detector 42).

The limiter 43 adjusts, in the slicing direction, the range of X-rays to which the patient O is exposed. The limiter 43 performs this adjustment under the control of the limiter driver 46. In other words, the limiter driver 46 adjusts the opening of the limiter 43 to change the range of X-ray exposure in the slicing direction.

The data acquisition system 44 is generally referred to as a DAS. The data acquisition system 44 amplifies a signal output from the X-ray detector 42 for each channel, and converts the amplified signal into a digital signal. The resulting raw data (RAW data) obtained by the conversion is supplied via the IF 49 of the imaging system 31 to the medical image processing apparatus 10 outside the imaging system 31.

The main controller 48 controls the data acquisition system 44, the high-voltage generator 45, the limiter driver 46, the rotation driver 47, and the table-top driver 51 on the basis of control signals input from the medical image processing apparatus 10 via the IF 49.

The table-top 50 is a table on which the patient O is placed.

The table-top driver 51 causes the table-top 50 to move in the slicing direction. The rotating unit R has an opening at the center, through which the patient O placed on the table-top 50 is inserted. Note that a direction parallel to the central rotation axis of the rotating unit R is defined as a Z-axis direction (slicing direction), and directions of planes orthogonal to the Z-axis direction are defined as an X-axis direction and a Y-axis direction.

Note that in the medical image processing apparatus 10 of the X-ray CT apparatus 30 shown in FIG. 7, components identical to those of the medical image processing apparatus 10 shown in FIG. 1 are assigned the same reference numerals and their description is omitted. The IF 17 shown in FIG. 7 is connected to the IF 49 of the imaging system 31 and communicates with the imaging system 31.

Figure 8:
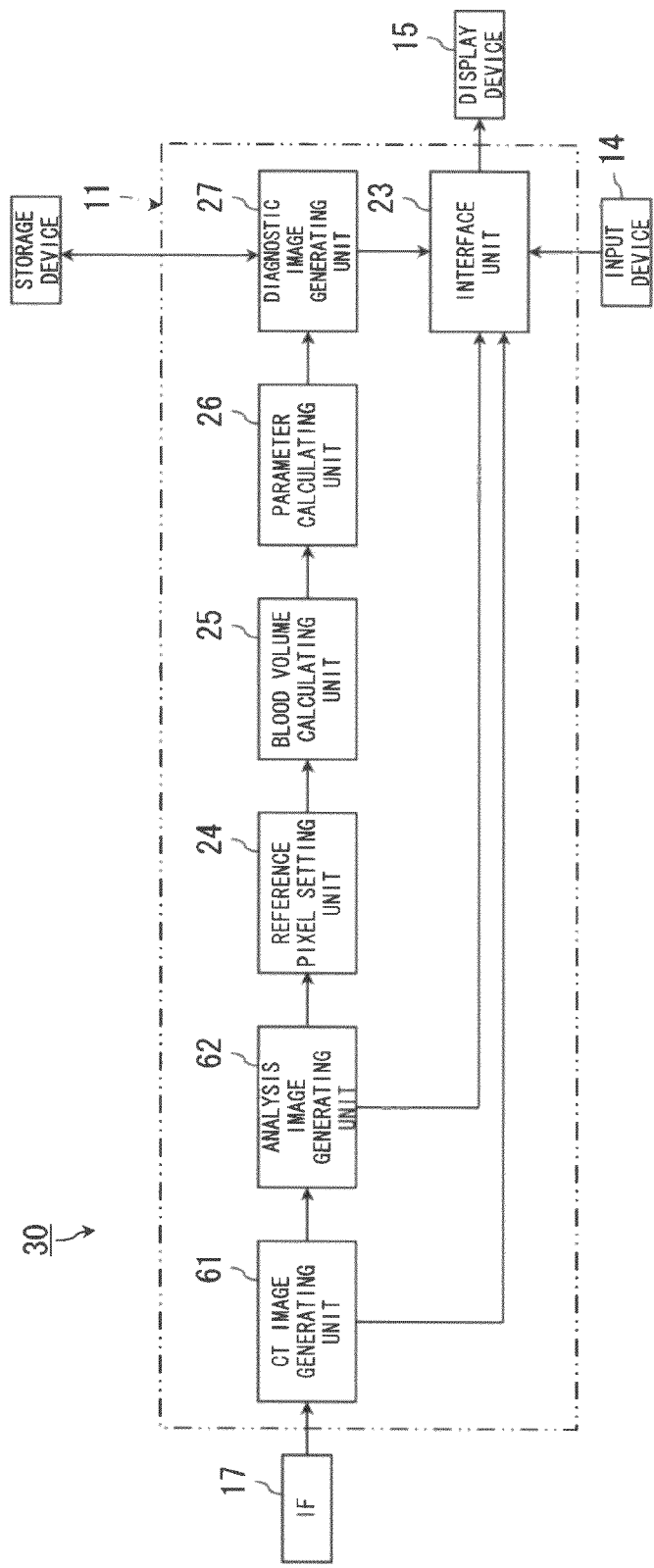
FIG. 8 is a block diagram showing functions of an X-ray CT apparatus including the medical image processing apparatus of the present embodiment.

FIG. 8 is a block diagram showing functions of the X-ray CT apparatus 30 including the medical image processing apparatus 10 of the present embodiment.

When the CPU 11 shown in FIG. 7 executes a program, the X-ray CT apparatus 30 of FIG. 8 functions as a CT image generating unit 61, an analysis image generating unit 62, the interface unit 23, the reference pixel setting unit 24, the blood volume calculating unit 25, the parameter calculating unit 26, and the diagnostic image generating unit 27. Alternatively, the X-ray CT apparatus 30 may include the CT image generating unit 61, the analysis image generating unit 62, the interface unit 23, the reference pixel setting unit 24, the blood volume calculating unit 25, the parameter calculating unit 26, and the diagnostic image generating unit 27 as a circuit.

To use the CT-perfusion technique, the CT image generating unit 61 controls the imaging system 31 to perform imaging of a liver of the patient O to which a contrast agent has been given, the liver being a target body part. Thus, the CT image generating unit 61 generates data of a plurality of time-series CT images of the liver of the patient O.

The analysis image generating unit 62 analyzes the data of the plurality of time-series CT images generated by the CT image generating unit 61, and generates a hepatic blood flow image, a hepatic blood volume image, a mean transit time image, and a hepatic arterial fraction image serving as functional images. The CT images generated by the CT image generating unit 61 and the functional images generated by the analysis image generating unit 62 are displayed via the interface unit 23 on the display device 15.

In the X-ray CT apparatus 30 shown in FIG. 8, components identical to those of the medical image processing apparatus 10 shown in FIG. 2 are assigned the same reference numerals and their description is omitted.

When the CPU 11 shown in FIG. 7 executes a program, the X-ray CT apparatus 30 may function as the CT image generating unit 61 shown in FIG. 8, the analysis image generating unit 22, the interface unit 23, the blood volume calculating unit 25A, the parameter calculating unit 26A, and the diagnostic image generating unit 27A shown in FIG. 5. Alternatively, when the CPU 11 shown in FIG. 7 executes a program, the X-ray CT apparatus 30 may function as the CT image generating unit 61 shown in FIG. 8, the analysis image generating unit 22, the interface unit 23, the parameter calculating unit 26B, and the diagnostic image generating unit 27B sown in FIG. 6.

The X-ray CT apparatus 30 including the medical image processing apparatus 10 of the present embodiment is capable of generating and displaying a visible diagnostic image of a liver in early stages of the multistage carcinogenic process, such as the regenerative nodule stage and the adenoma stage. It is thus possible to achieve improved accuracy in diagnosing hepatocellular cancer.

What is claimed is:

1. A medical image processing apparatus, comprising:
a processor configured to
analyze data of a plurality of time-series medical images, each containing an image of an organ having a functional blood vessel and a feeding blood vessel;
calculate a parameter based on at least a blood volume in the feeding blood vessel;
obtain a degree of the cancer progression corresponding to the calculated parameter by referring to a table which associates in advance parameters with degrees of a cancer progression of the organ; and
generate an image to which the obtained degree is applied on a region-by-region basis, wherein
the processor is further configured to
set a reference region on a functional image obtained by analyzing the data of the medical images;
calculate the blood volume in the functional blood vessel and a blood volume in the feeding blood vessel for the reference region, and to calculate the blood volume in the functional blood vessel and the blood volume in the feeding blood vessel for a non-reference region on the functional image, the non-reference region not being the reference region; and
calculate a combination of a first comparison value by comparing the blood volume in the functional blood vessel calculated for the reference region and the blood volume in the functional blood vessel calculated for the non-reference region, and a second comparison value by comparing the blood volume in the feeding blood vessel calculated for the reference region and the blood volume in the feeding blood vessel calculated for the non-reference region as the parameter, and
the table associates combinations as the parameters with the degrees of the cancer progression of the organ.

2. The medical image processing apparatus according to claim 1, wherein
the processor is configured to analyze the data of the medical images, each containing the image of the organ having a portal vein as the functional blood vessel and a hepatic artery as the feeding blood vessel.

3. The medical image processing apparatus according to claim 1, wherein
the functional image is a friction image indicating a friction of the blood volume in the feeding blood vessel.

4. The medical image processing apparatus according to claim 1, wherein
the processor is further configured to calculate the first comparison value, which is a ratio between the blood volume in the functional blood vessel calculated for the reference region and the blood volume in the functional blood vessel calculated for the non-reference region, and the second comparison value, which is a ratio between the blood volume in feeding blood vessel calculated for the reference region and the blood volume in the feeding blood vessel calculated for the non-reference region.

5. The medical image processing apparatus according to claim 1, wherein
the processor is further configured to calculate the first comparison value, which is a difference between the blood volume in the functional blood vessel calculated for the reference region and the blood volume in the functional blood vessel calculated for the non-reference region, and the second comparison value, which is a difference between the blood volume in the feeding blood vessel calculated for the reference region and the blood volume in the feeding blood vessel calculated for the non-reference region.

6. The medical image processing apparatus according to claim 1, wherein
the processor is further configured to set a reference pixel included in a group of pixels constituting the functional image as the reference region, and
calculate the blood volume in the functional blood vessel and the blood volume in the feeding blood vessel corresponding to the reference pixel, and calculate the blood volume in the functional blood vessel and the blood volume in the feeding blood vessel corresponding to a non-reference pixel included in the group of pixels constituting the functional image as the non-reference region.

7. The medical image processing apparatus according to claim 1, wherein the processor is further configured to set the reference region and the non-reference region by converting a first region and a second region selected on a 3D image or a multi-planar reconstruction image serving as a medical image into those on the functional image.

8. The medical image processing apparatus according to claim 1, wherein
the data of the medical images is data of X-ray CT images, MRI images, or ultrasound images.

9. An X-ray CT apparatus comprising the medical image processing apparatus according to claim 1.

10. An MRI apparatus comprising the medical image processing apparatus according to claim 1.

11. An ultrasound diagnostic imaging apparatus comprising the medical image processing apparatus according to claim 1.

12. A medical image processing apparatus comprising:
a processor configured to
analyze data of a plurality of time-series medical images, each containing an image of an organ having a functional blood vessel and a feeding blood vessel;
calculate a parameter based on at least a blood volume in the feeding blood vessel;
obtain a degree of the cancer progression corresponding to the calculated parameter by referring to a table which associates in advance parameters with degrees of a cancer progression of the organ; and
generate an image to which the obtained degree is applied on a region-by-region basis, wherein
the processor is further configured to calculate a product of the blood volume in the functional blood vessel and a blood volume in the feeding blood vessel as the parameter, and
the table associates products as the parameters with the degrees of the cancer progression of the organ.

13. A medical image processing method, comprising:
a parameter calculating step of analyzing data of a plurality of time-series medical images, each containing an image of an organ having a functional blood vessel and a feeding blood vessel and calculating a parameter based on at least a blood volume in the feeding blood vessel; and
an image generating step of obtaining a degree of the cancer progression corresponding to the calculated parameter by referring to a table which associates in advance parameters with degrees of a cancer progression of the organ and generating an image to which the obtained degree is applied on a region-by-region basis, wherein
the parameter calculating step calculates a product of the blood volume in the functional blood vessel and a blood volume in the feeding blood vessel as the parameter, and
the table associates products as the parameters with the degrees of the cancer progression of the organ.

14. A medical image processing method, comprising:
a parameter calculating step of analyzing data of a plurality of time-series medical images, each containing an image of an organ having a functional blood vessel and a feeding blood vessel and calculating a parameter based on at least a blood volume in the feeding blood vessel; and
an image generating step of obtaining a degree of the cancer progression corresponding to the calculated parameter by referring to a table which associates in advance parameters with degrees of a cancer progression of the organ and generating an image to which the obtained degree is applied on a region-by-region basis, wherein
the parameter calculating step includes
a reference region setting step of setting a reference region on a functional image obtained by analyzing the data of the medical images;
a blood volume calculating step of calculating the blood volume in the functional blood vessel and a blood volume in the feeding blood vessel for the reference region, and of calculating the blood volume in the functional blood vessel and the blood volume in the feeding blood vessel for a non-reference region on the functional image, the non-reference region not being the reference region; and
a comparison value calculating step of calculating a combination of a first comparison value by comparing the blood volume in the functional blood vessel calculated for the reference region and the blood volume in the functional blood vessel calculated for the non-reference region, and a second comparison value by comparing the blood volume in the feeding blood vessel calculated for the reference region and the blood volume in the feeding blood vessel calculated for the non-reference region as the parameter, and
the table associates combinations as the parameters with the degrees of the cancer progression of the organ.

15. The medical image processing method according to claim 14, wherein
the functional image is a friction image indicating a friction of the blood volume in the feeding blood vessel.

16. The medical image processing method according to claim 14, wherein
the comparison value calculating step calculates the first comparison value which is a ratio between the blood volume in the functional blood vessel calculated for the reference region and the blood volume in the functional blood vessel calculated for the non-reference region, and the second comparison value which is a ratio between the blood volume in feeding blood vessel calculated for the reference region and the blood volume in the feeding blood vessel calculated for the non-reference region.

17. The medical image processing method according to claim 14, wherein
the comparison value calculating step calculates the first comparison value which is a difference between the blood volume in the functional blood vessel calculated for the reference region and the blood volume in the functional blood vessel calculated for the non-reference region, and the second comparison value which is a difference between the blood volume in the feeding blood vessel calculated for the reference region and the blood volume in the feeding blood vessel calculated for the non-reference region.

18. The medical image processing method according to claim 14, wherein the reference region setting step sets a reference pixel included in a group of pixels constituting the functional image as the reference region, and the blood volume calculating step calculates the blood volume in the functional blood vessel and the blood volume in the feeding blood vessel corresponding to the reference pixel, and calculates the blood volume in the functional blood vessel and the blood volume in the feeding blood vessel corresponding to a non-reference pixel included in the group of pixels constituting the functional image as the non-reference region.

* * * * *